United States Patent
Xing et al.

(10) Patent No.: US 11,213,615 B2
(45) Date of Patent: *Jan. 4, 2022

(54) COMPOSITION FOR SUBMUCOSAL INJECTION, REAGENT COMBINATION, AND APPLICATIONS THEREOF

(71) Applicant: EndoClot Plus Co., Ltd, Suzhou (CN)

(72) Inventors: Cheng Xing, Suzhou (CN); Xin Ji, Suzhou (CN); Heng Zhang, Suzhou (CN)

(73) Assignee: EndoClot Plus Co.. Ltd, Suzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/487,764

(22) PCT Filed: Feb. 26, 2018

(86) PCT No.: PCT/CN2018/077201
§ 371 (c)(1),
(2) Date: Aug. 21, 2019

(87) PCT Pub. No.: WO2018/157772
PCT Pub. Date: Sep. 7, 2018

(65) Prior Publication Data
US 2019/0381217 A1    Dec. 19, 2019

(30) Foreign Application Priority Data
Feb. 28, 2017  (CN) .......................... 201710112247.6

(51) Int. Cl.
| A61L 31/16 | (2006.01) |
| C08K 5/053 | (2006.01) |
| C08L 3/02  | (2006.01) |
| A61L 31/04 | (2006.01) |

(52) U.S. Cl.
CPC ............. *A61L 31/042* (2013.01); *A61L 31/16* (2013.01); *C08K 5/053* (2013.01); *C08L 3/02* (2013.01); *A61L 2300/232* (2013.01); *A61L 2400/06* (2013.01); *C08L 2203/02* (2013.01)

(58) Field of Classification Search
None
See application file for complete search history.

(56) References Cited

U.S. PATENT DOCUMENTS

| 471,865 A   | 3/1892  | Howard     |
| 576,437 A   | 2/1897  | Elliott    |
| 881,238 A   | 3/1908  | Sayer      |
| 1,685,280 A | 9/1928  | Findley    |
| 1,732,566 A | 10/1929 | Mckendrick |
| 1,934,793 A | 11/1933 | Crain      |
| 2,122,234 A | 6/1938  | Joseph     |
| 2,151,418 A | 3/1939  | Bolte      |
| 2,185,927 A | 1/1940  | Shelanski  |
| 2,570,774 A | 10/1951 | Frank      |
| 3,419,006 A | 12/1968 | Paula      |
| 4,184,258 A | 1/1980  | Barrington |
| 4,616,644 A | 10/1986 | Saferstein |
| 5,273,531 A | 12/1993 | Knoepfler  |
| 5,312,331 A | 5/1994  | Knoepfler  |
| 5,445,612 A | 8/1995  | Terakura   |
| 5,599,297 A | 2/1997  | Chin       |
| 5,800,381 A | 9/1998  | Ognier     |
| 5,874,500 A | 2/1999  | Rhee       |
| 5,951,531 A | 9/1999  | Ferdman    |
| 6,312,725 B1 | 11/2001 | Wallace   |
| 6,610,005 B1 | 8/2003  | Tao        |
| 7,427,607 B2 | 9/2008  | Suzuki     |
| 7,547,292 B2 | 6/2009  | Sheldrake  |
| 8,575,132 B2 | 11/2013 | Ji         |
| 8,721,582 B2 | 5/2014  | Ji         |
| 8,827,980 B2 | 9/2014  | Ji         |
| 8,912,168 B2* | 12/2014 | Ji ........................ A61K 31/718 514/60 |
| 9,533,005 B2* | 1/2017 | Ji ............................ C08B 33/02 |
| 9,629,966 B2 | 4/2017 | Ji |
| 9,687,501 B2* | 6/2017 | Ji ............................ C08B 33/06 |
| 10,076,590 B2* | 9/2018 | Ji ........................ A61K 9/0014 |
| 10,195,312 B2* | 2/2019 | Ji ............................ C08B 33/04 |
| 2003/0181917 A1 | 9/2003 | Gertner |
| 2004/0096507 A1 | 5/2004 | Kwang |
| 2008/0021374 A1 | 1/2008 | Kawata |
| 2008/0214989 A1 | 9/2008 | Kawata |
| 2009/0062233 A1 | 3/2009 | Ji |
| 2010/0035886 A1 | 2/2010 | Cincotta |

(Continued)

FOREIGN PATENT DOCUMENTS

| CA | 2599082 A1  | 2/2009  |
| CN | 86103931 A  | 12/1986 |

(Continued)

OTHER PUBLICATIONS

ISA, International Search Report and Written Opinion for International Patent Application No. PCT/CN2018/077201 with English translation. dated May 30, 2018. 10 pages.

(Continued)

*Primary Examiner* — Alton N Pryor
(74) *Attorney, Agent, or Firm* — Novel IP (57) ABSTRACT

Described herein is a composition for submucosal injection comprises a biocompatible modified starch and a pharmaceutically acceptable carrier for injection. The biocompatible modified starch is in an amount ranging from 0.2 wt % to 50 wt % of the total weight of composition. The biocompatible modified starch is selected from one or more of the group consisting of: etherified starches, esterified starches, cross-linked starches, pre-gelatinized starches, graft starches and composite modified starches, which has a molecular weight ranging from 3,000 to 2,000,000 daltons, a water absorbency capability of at least twice of its own weight, and a particle size from 500 nm to 1000 μm. The viscosity of the composition ranges from 9 mPa·s to 150,000 mPa·s at 25° C. The present disclosure also provides a combination reagent for submucosal injection, comprising the above-mentioned biocompatible modified starch and the pharmaceutically acceptable carrier for injection.

40 Claims, 1 Drawing Sheet

(56) References Cited

U.S. PATENT DOCUMENTS

| | | |
|---|---|---|
| 2010/0331232 A1 | 12/2010 | Barker |
| 2011/0066132 A1 | 3/2011 | Ji |
| 2011/0178495 A1 | 7/2011 | Ji |
| 2011/0208158 A1 | 8/2011 | Sigmon, Jr. et al. |
| 2011/0224724 A1 | 9/2011 | Lu |
| 2013/0046278 A1 | 2/2013 | Ji |
| 2013/0108671 A1 | 5/2013 | Mccoy |
| 2013/0123213 A1 | 5/2013 | Ji |
| 2013/0131621 A1 | 5/2013 | Van Holten |
| 2013/0255538 A1 | 10/2013 | Lu |
| 2014/0207097 A1 | 7/2014 | Ji |
| 2015/0297520 A1* | 10/2015 | Kobiki .............. A61K 9/2077 424/489 |
| 2015/0359925 A1 | 12/2015 | Wang |
| 2017/0252479 A1 | 9/2017 | Ji |

FOREIGN PATENT DOCUMENTS

| | | |
|---|---|---|
| CN | 1451667 A | 10/2003 |
| CN | 101091803 A | 12/2007 |
| CN | 101121041 A | 2/2008 |
| CN | 101361986 A | 2/2009 |
| CN | 101455857 A | 6/2009 |
| CN | 101485897 A | 7/2009 |
| CN | 101497670 A | 8/2009 |
| CN | 101785873 A | 7/2010 |
| CN | 102019028 B | 4/2011 |
| CN | 102762244 A | 10/2012 |
| CN | 103957947 A | 7/2014 |
| CN | 103957948 A | 7/2014 |
| CN | 103957949 A | 7/2014 |
| CN | 103957954 A | 7/2014 |
| CN | 104689380 A | 6/2015 |
| CN | 105412975 A | 3/2016 |
| CN | 105536039 A | 5/2016 |
| CN | 105688265 A * | 6/2016 |
| CN | 106267379 A | 1/2017 |
| CN | 106474529 A | 3/2017 |
| CN | 106729775 A | 5/2017 |
| CN | 106806936 A | 6/2017 |
| CN | 107349436 A | 11/2017 |
| EP | 0206697 A2 | 12/1986 |
| EP | 1523994 A1 | 4/2005 |
| EP | 2617792 A2 | 7/2013 |
| EP | 3228331 A1 | 10/2017 |
| JP | WO2014030656 A * | 2/2014 |
| JP | 2017527416 A | 9/2017 |
| KR | 20140100245 A | 8/2014 |
| KR | 20170060054 A | 5/2017 |
| WO | 2012006427 A1 | 1/2012 |
| WO | 2016041443 A1 | 3/2016 |
| WO | 2018157772 A1 | 9/2018 |
| WO | 2020020114 A1 | 1/2020 |

OTHER PUBLICATIONS

International Search Report for PCT/CN2015/088844, dated Dec. 8, 2015.
Natour et al., "Assessment of the effect on blood loss and transfusion requirements when adding a polyethylene glycol sealant to the anastomotic closure of aortic procedures: a case-control analysis of 102 patients undergoing Bentall procedures" J Cardiothorac Surg. 2012; 7: 105. Published online Oct. 8, 2012. doi: 10.1186/1749-8090-7-105.
Database WP1 Week 201068 Thomson Scientific, London, GB; An 2010-K65387 XP002784440, & CN101785873A (JI X) Jul. 28, 2010.
N. N. : "Polyox TM WSR 301 Amerchol", The Dow Chemical Company Sales Specification, 2012, XP002784406.
N. N. : "Polyox TM Water Soluble Resins", DOW, Oct. 2013, XP002784441.
International Search Report for PCT/CN2019/071108, dated Apr. 8, 2019.
International Search Report for PCT/CN2019/097177, dated Oct. 29, 2019.

* cited by examiner

COMPOSITION FOR SUBMUCOSAL INJECTION, REAGENT COMBINATION, AND APPLICATIONS THEREOF

CROSS REFERENCE TO RELATED APPLICATIONS

The present application claims the benefit of, and the priority to, Chinese Patent Application Serial No. 201710112247.6, filed on Feb. 28, 2017, entitled "COMPOSITION FOR SUBMUCOSAL INJECTION, REAGENT COMBINATION, AND APPLICATIONS THEREOF", the disclosure of which is hereby incorporated by reference in its entirety.

FIELD OF THE INVENTION

The present disclosure relates to a composition and combination reagents for submucosal injection, which comprise biocompatible modified starches, and applications thereof.

BACKGROUND OF THE INVENTION

Endoscopic Mucosal Resection (EMR) and Endoscopic Submucosal Dissection (ESD) are primary minimally invasive therapies for early gastrointestinal cancer and precancerous lesions. Submucosal injection is required to perform EMR and ESD, which comprises injecting fluid into the submucosal sites to form a submucosal fluid cushion (SFC) between the lesion mucosa and the smooth muscle layer. The submucosal fluid cushion serves as a submucosal isolation layer to lift up the lesion mucosa and separate the mucosal layer from the muscle layer. When the lesion mucosa is resected by an electrosurgical knife, coagulation caused by high-frequency current is limited to the mucosal layer, so as to protect the muscle layer and the underneath tissues thereof from being destroyed to avoid occurrence of complications such as perforation and the like. In recent years, most of bladder tumors can be resected through minimally invasive surgeries under endoscopy (cystoscopy). Resection of bladder tumors under endoscopy for example using EMR or ESD may cause complications such as bladder perforation. Therefore, before resection of bladder tumors under endoscopy, it is necessary to inject a certain amount of physiological saline into the submucosal sites at the base of the tumor to separate the mucosa from the bladder muscle layer, so as to avoid bladder perforation during operation.

Theoretically, the longer the time period SCF lasts, the less time the operation takes and the less complications occur. EMR and ESD are usually performed in combination with submucosal injection. Therefore, submucosal injection is a critical factor to ensure the safety of surgery.

The ideal submucosal injection fluid should have the following features:
  (i) capable of forming SFC with certain thickness (height) which satisfies surgical needs;
  (ii) allowing SFC to last for a sufficient time period to perform surgery;
  (iii) good biocompatibility with tissues, without damage to tissues;
  (iv) reasonable cost The submucosal injection fluid existing in the prior arts comprises physiological saline, glucose, glycerin, fructose, sodium hyaluronate, and hydroxymethyl cellulose, etc. The submucosal injection fluid that is commonly used is physiological saline. However, the physiological saline is unsatisfactory in terms of height of the formed submucosal fluid cushion and duration for which the cushion lasts, because the physiological saline would rapidly diffuse to the surrounding tissues under mucosa. Since the SFC formed by physiological saline has a low height, it's difficult to perform resection and there is high possibility of damaging the muscle layer and causing complications during the resection. Some other substances, such as glycerin and fructose, may be used to replace physiological saline for submucosal injection. However, these substances exhibit the following disadvantages: a) the formed cushion cannot last for a sufficient time period; b) excessive local concentration is harmful to the tissues; c) it is difficult to perform injection through a universal digestive tract mucosal syringe and a bladder mucosal syringe (including a catheter and an injection needle) under endoscopy due to their high viscosity. The local cushions formed by sodium hyaluronate injection cannot last for a long time period. Since hyaluronic acid comprises stimulation tumor growth factors and may lead to risk of tumor cells proliferation due to residual hyaluronic acid at local wound surface, and the use of hyaluronic acid may lead to high cost, the clinical use of hyaluronic acid is not widely available. There are only reports about the use of the above submucosal injections under the digestive tract endoscope. Only physiological saline has recently been used for resection of tumors under cystoscope in clinical practice, but no other substance is reported. U.S. Patent Application No. US20110208158A1 describes utilization of carboxymethyl cellulose (CMC) (a species of cellulose materials) for submucosal injection, which is gradually degraded by phagocytosis of phagocytic cells in human body. It takes several weeks or even months to fully degrade cellulose materials in human body, which may cause local tissue hyperplasia and affect tissue healing.

In addition, it has been reported that under the digestive tract endoscope, doctors use plasma substitutes for submucosal injection. Some of these plasma substitutes comprise hydroxyethyl starch, which is a soluble starch that forms a homogeneous solution in water. Hydroxyethyl starch is served as plasma substitutes and delivered directly to the blood vessels of patients suffering from severe blood loss. Since the concentration and formulation of the plasma substitutes are set by the manufacturer to replace human plasma, there are many limitations for submucosal application. For example, it is difficult for a doctor to select and control the viscosity, molecular weight, and water absorbency capability of plasma substitutes according to clinical needs. After homogeneous solution of hydroxyethyl starch is injected into submucosal sites, it would easily diffuse toward surrounding tissues along the connective tissue between the submucosa and the muscle layer, thereby resulting in insufficient thickness of the local SFC and short lasting of SFC. Therefore, the use of plasma substitutes cannot meet the surgical requirements.

Therefore, there is a need for a novel composition for submucosal injection to replace the existing materials.

SUMMARY OF THE INVENTION

In one aspect, provided herein is a composition for submucosal injection, comprising: a biocompatible modified starch in an amount ranging from 0.2 wt % to 50 wt % of the total weight of the composition, and a pharmaceutically acceptable carrier for injection. The biocompatible modified starch is selected from one or more of the group consisting of etherified starches, esterified starches, cross-linked starches, pre-gelatinized starches, graft starches and composite modified starches, which has a molecular weight ranging from 3,000 to 2,000,000 daltons, a water absorbency capability of at least twice of its own weight, and a particle size ranging from 500 nm to 1000 µm. Further, the composition has a viscosity from 9 mPa·s to 150,000 mPa·s at 25° C.

In some embodiments, the pharmaceutically acceptable carrier for injection is selected from one or more of the group consisting of: physiological saline, balanced salt solution, glucose solution, sterile pyrogen-free water, and glycerin.

In some embodiments, the etherified starches comprise a carboxymethyl starch and a salt thereof; the esterified starches comprise a carboxymethyl starch and a salt thereof; the cross-linked starches comprise a cross-linked carboxymethyl starch and a salt thereof; the pre-gelatinized starches comprise a pre-gelatinized hydroxypropyl starch diphosphate; the graft starches comprise a propylene ester-carboxymethyl starch grafted copolymer and an acrylic acid-carboxymethyl starch grafted copolymer; the composite modified starches comprise a pre-gelatinized hydroxypropyl starch diphosphate. The above-mentioned biocompatible modified starch has a molecular weight ranging from 3,000 to 200,000 daltons, or 5,000 to 100,000 daltons, or 5,000 to 50,000 daltons, a water absorbency capability ranging from 2 to 100 times, or 5 to 75 times, or 5 to 50 times, or 2 to 10 times, or 2 to 5 times of its own weight, and a particle size ranging from 1 to 500 µm, or 1 to 1000 µm, or 10 to 1000 µm. And the above-mentioned biocompatible modified starch is degradable by amylases and/or amylases.

In some embodiments, the above-mentioned biocompatible modified starch is in an amount ranging from 0.2 wt % to 20 wt %, or 0.5 wt % to 10 wt %, or 0.5 wt % to 5 wt %, or 1 wt % to 5 wt %, or 0.5 wt % to 1.5 wt %, or 2 wt % to 6 wt % of the total weight of the composition. The viscosity of the composition at 25° C. ranges from 9 mPa·s to 100,000 mPa·s, or 9 mPa·s to 10,000 mPa·s, or 9 mPa·s to 5,000 mPa·s, or 9 mPa·s to 1,000 mPa·s.

In some embodiments, the mucosa comprises digestive tract mucosa, respiratory mucosa, genital tract mucosa or urinary tract mucosa. The digestive tract mucosa comprises esophageal tract mucosa or gastrointestinal tract mucosa. The respiratory mucosa comprises nasal mucosa, laryngeal mucosa, oral mucosa, trachea or bronchial mucosa. The urinary tract mucosa comprises a urethral mucosa or a bladder mucosa. The genital mucosa comprises vaginal mucosa or uterine mucosa.

In some embodiments of the composition for submucosal injection, the biocompatible modified starch is a carboxymethyl starch sodium in an amount ranging from 1 wt % to 25 wt % of the total weight of the composition, and the pharmaceutically acceptable carrier for injection is physiological saline.

In some embodiments of the composition for submucosal injection, the biocompatible modified starch is a pre-gelatinized hydroxypropyl starch diphosphate in an amount ranging from 0.5 wt % to 25 wt % of the total weight of the composition, and the pharmaceutically acceptable carrier for injection is physiological saline.

In some embodiments of the composition for submucosal injection, the biocompatible modified starch is a cross-linked carboxymethyl starch sodium in an amount ranging from 0.5 wt % to 20 wt % of the total weight of the composition, and the pharmaceutically acceptable carrier for injection is physiological saline.

In other embodiments, the composition for submucosal injection as described herein further comprises coloring agents and/or other drugs. The coloring agents can be selected according to doctor's habits and actual clinical needs, such as but not limited to, methylene blue and indigo dyes. The said other drugs comprise, such as but not limited to: one or more of a vasoconstrictor drug, an antibacterial drug, an anti-inflammatory drug, and an antitumor drug.

In another aspect, provided herein is use of the biocompatible modified starch in manufacturing a submucosal injection formulation. The biocompatible modified starch is selected from one or more of the group consisting of etherified starches, esterified starches, cross-linked starches, pre-gelatinized starches, graft starches, and composite modified starches, which has a molecular weight ranging from 3,000 to 2,000,000 daltons, a water absorbency capability of at least twice of its own weight, and a particle size ranging from 500 nm to 1000 µm. And the aqueous solution of the biocompatible modified starch with a concentration less than 6.67% has a viscosity that is not less than 34 mPa·s at 37° C. The biocompatible modified starch is degradable by amylases and/or amylases.

In some embodiments, the submucosal injection formulation comprises the above-mentioned biocompatible modified starch in an amount ranging from 0.2 wt % to 50 wt % of the total weight of the formulation and a pharmaceutically acceptable carrier for injection. The viscosity of the submucosal injection formulation ranges from 9 mPa·s to 150,000 mPa·s at 25° C. The pharmaceutically acceptable carrier for injection is selected from one or more of the group consisting of: physiological saline, balanced salt solution, glucose solution, sterile pyrogen-free water, and glycerin.

In some embodiments, the etherified starches comprise carboxymethyl starch and a salt thereof; the esterified starches comprise carboxymethyl starch and a salt thereof; the cross-linked starches comprise cross-linked carboxymethyl starch and a salt thereof; the pre-gelatinized starches comprise pre-gelatinized hydroxypropyl starch diphosphate; the graft starches comprise propylene ester-carboxymethyl starch grafted copolymer and acrylic acid-carboxymethyl starch grafted copolymer; the composite modified starches comprise pre-gelatinized hydroxypropyl starch diphosphate. 1% aqueous solution of the above-mentioned biocompatible modified starch has a viscosity that is not less than 34 mPa·s at 37° C., or 2% aqueous solution of the above-mentioned biocompatible modified starch has a viscosity that is not less than 34 mPa·s at 37° C., or 3% aqueous solution of the above-mentioned biocompatible modified starch has a viscosity that is not less than 34 mPa·s at 37° C. The above-mentioned biocompatible modified starch has a molecular weight ranging from 3,000 to 200,000 daltons, or 5,000 to 100,000 daltons, or 5,000 to 50,000 daltons, a water absorbency capability ranging from 2-100 times, or 5-75 times, or 5-50 times, or 2-10 times, or 2- 5 times of its own weight, and a particle size ranging from 1µm to 500 µm, or 1µm to 1000 µm, or 10 µm to 1000 µm.

In some embodiments, the above-mentioned biocompatible modified starch is in an amount ranging from 0.2 wt % to 20 wt %, or 0.5 wt % to 10 wt %, or 0.5 wt % to 5 wt %, or 1 wt % to 5 wt %, or 0.5 wt % to 1.5 wt %, or 2 wt % to 6 wt % of the total weight of the submucosal injection formulation. And, the viscosity of the submucosal injection formulation at 25° C. ranges from 9 mPa·s to 100,000 mPa·s, or 9 mPa·s to 10,000 mPa·s, or 9 mPa·s to 5,000 mPa·s, or 9 mPa·s to 1,000 mPa·s.

In yet another aspect, provided herein is a combination for submucosal injection, comprising: a biocompatible modified starch and a pharmaceutically acceptable carrier for injection. The biocompatible modified starch is selected from one or more of the group consisting of: etherified starches, esterified starches, cross-linked starches, pre-gelatinized starches, graft starches and composite modified starches, which has a molecular weight ranging from 3,000 to 2,000,000 daltons, a water absorbency capability of at least twice of its own weight, and a particle size from 500 nm to 1000 μm. Moreover, the biocompatible modified starch is degradable by amylases and/or amylases. The biocompatible modified starch in an amount ranging from 0.2 wt % to 50 wt % of the total weight is mixed with the said carrier to form a viscous composition, which has a viscosity ranging from 9 mPa·s to 150,000 mPa·s at 25° C.

In some embodiments, the pharmaceutically acceptable carrier for injection is selected from one or more of the group consisting of: physiological saline, balanced salt solution, glucose solution, sterile pyrogen-free water, and glycerin.

In some embodiments, the etherified starches comprise carboxymethyl starch and a salt thereof; the esterified starches comprise carboxymethyl starch and a salt thereof; the cross-linked starches comprise cross-linked carboxymethyl starch and a salt thereof; the pre-gelatinized starches comprise pre-gelatinized hydroxypropyl starch diphosphate; the graft starches comprise propylene ester-carboxymethyl starch grafted copolymer and acrylic acid-carboxymethyl starch grafted copolymer; the composite modified starches comprise pre-gelatinized hydroxypropyl starch diphosphate. The above biocompatible modified starch has a molecular weight ranging from 3,000 to 200,000 daltons, or 5,000 to 100,000 daltons, or 5,000 to 50,000 daltons, a water absorbency capability of 2-100 times, or 5-75 times, or 5-50 times, or 2-10 times, or 2- 5 times of its own weight, and a particle size ranging from 1μm to 500 μm, or 1μm to 1000 μm, or 10 um to 1000 μm.

In some embodiments, the above-mentioned biocompatible modified starch is in an amount ranging from 0.2 wt % to 20 wt %, or 0.5 wt % to 10 wt %, or 0.5 wt % to 5 wt %, or 1 wt % to 5 wt %, or 0.5 wt % to 1.5 wt %, or 2 wt % to 6 wt % of the total weight. And, the viscosity of the formed viscous composition ranges from 9 mPa·s to 100,000 mPa·s, or 9 mPa·s to 10,000 mPa·s, or 9 mPa·s to 5,000 mPa·s, or 9 mPa·s to 1,000 mPa·s at 25° C.

In one embodiment of the combination for submucosal injection, the biocompatible modified starch is carboxymethyl starch sodium, and the pharmaceutically acceptable carrier for injection is physiological saline. The carboxymethyl starch sodium in an amount ranging from 1 wt % to 25 wt % of the total weight of the combination is mixed with the physiological saline.

In one embodiment of the combination for submucosal injection, the biocompatible modified starch is pre-gelatinized hydroxypropyl starch diphosphate, and the pharmaceutically acceptable carrier for injection is physiological saline. The pre-gelatinized hydroxypropyl starch diphosphate in an amount ranging from 0.5 wt % to 25 wt % of the total weight of the combination is mixed with the physiological saline.

In one embodiment of the combination for submucosal injection, the biocompatible modified starch is cross-linked carboxymethyl starch sodium, and the pharmaceutically acceptable carrier for injection is physiological saline. The cross-linked carboxymethyl starch sodium in an amount ranging from 0.5 wt % to 20 wt % of the total weight is mixed with the physiological saline.

In other embodiments, the combination for submucosal injection as described herein further comprises coloring agents and/or other drugs. The coloring agents can be selected according to doctor's habits and actual clinical needs, such as but not limited to, methylene blue and indigo dyes. The said other drugs comprise, such as but not limited to: one or more of a vasoconstrictor drug, an antibacterial drug, an anti-inflammatory drug, and an antitumor drug.

In still another aspect, provided herein is an apparatus for delivering the composition for submucosal injection, comprising: a hollow housing having a hollow portion for receiving an injection to be delivered, and proximal and distal ends; a plunger disposed within the hollow portion, a plunger rod coupled to the plunger, and a plunger drive mechanism having a first arm and a second arm pivotally coupled to each other. The plunger rod is able to drive the plunger to reciprocatingly move in the hollow portion, such that the injection can be delivered out of the distal end of the housing from the hollow portion. The plunger drive mechanism forces the plunger rod to drive the plunger to reciprocatingly move in the hollow portion when the first arm and the second arm rotate relative to each other.

In some embodiments, both the first and second arms have a proximal end and a distal end. The distal end of the first arm is coupled to the proximal end of the housing. The distal end of the second arm is coupled to the proximal end of the plunger rod. When the first arm and the second arm are pivoted to drive the proximal ends of the first and second arms to move in a direction of facing each other, the second arm forces the plunger rod to drive the plunger to move to the distal end in the hollow portion.

In some embodiments, the first arm and the second arm are coupled to each other by a resilient spring, such that the first arm and the second arm can move back to the initial position after the proximal ends of the first and second arms move in a direction of facing each other to force the plunger rod to drive the plunger to move in the hollow portion of the housing.

In some embodiments, the plunger rod is provided with a thread scale for measuring the amount of the formulation delivered.

In still another aspect, provided herein is a kit for submucosal injection, comprising the composition for submucosal injection provided herein and the above-mentioned apparatus, or comprising a combination provided herein and the above-mentioned apparatus.

In still another aspect, provided herein is a method for lifting up a first tissue layer away from a second tissue layer, comprising delivering the composition for submucosal injection as described herein into the first tissue layer with the apparatus for delivering the composition for submucosal injection as described herein, to lift up the first tissue layer away from the second tissue layer.

For example, the composition for submucosal injection as described herein can be injected into submucosal sites with the apparatus for delivering the composition for submucosal injection as described herein via endoscopes (e.g., gastroscopes, colonoscopes, cystoscopes, etc.), such that a submucosal fluid cushion is formed to separate the mucosal layer from the submucosal tissue, followed by endoscopic minimally invasive surgery, such as EMR, ESD, or bladder tumor resection. The mucosa comprises digestive tract mucosa, respiratory mucosa, genital tract mucosa or urinary tract mucosa.

DETAILED DESCRIPTION OF THE INVENTION

Definition

The term "biocompatibility" or "biocompatible" as used herein refers to ability of tissues in a living body to perform an appropriate response to an inactive material. Generally, it refers to the compatibility of the materials with the host. Evaluation on biocompatibility mainly follows biosafety principles, i.e., elimination of injurious effect of biological materials on human tissues and organs, such as allergenicity, cytotoxicity and carcinogenicity. In addition, according to the sites on which the biological materials are to be applied, after the biological materials are directly used on the tissues and organs in the human body, they are required to be degraded and/or absorbed by organisms and tissues. Since the composition for submucosal injection as described herein is used for submucosal injection, that is, it is directly injected into the mucosa tissues, the biocompatibility especially refers to the absorbability and non-allergenicity of the materials in full compliance with biosafety principles.

The term "water absorbency capability" as used herein refers to the ratio between the mass or volume of water absorbed by unit mass or volume of the water absorbent and the volume or mass of the water absorbent.

The term "mucosa" as used herein refers to a layer of mucosal tissues within the organs such as the digestive tract (including mouth, stomach, intestines, etc.), respiratory tract, genital tract and urinary tract. The mucosal tissues have blood vessels and nerves distributed therein and can secrete mucus. The mucosa as described herein comprises digestive tract mucosa, respiratory tract mucosa, genital tract mucosa or urinary tract mucosa and so on.

The term "pharmaceutically acceptable carrier for injection" as used herein means that the carrier does not produce any toxic or adverse side effects after applying to a human, and is compatible with the active ingredients dissolved and/or suspended and/or complexed and/or mixed therein. The term "pharmaceutically acceptable carrier for injection" includes any and all solvents, dispersion media, isotonic agents, excipients, and the like, which are known to those of ordinary skill in the art, and combinations thereof.

For the operator who operates the apparatus for delivering the composition for submucosal injection as described herein, the "proximal end" used herein refers to the portion that is close to the operator.

For the operator who operates the apparatus for delivering the composition for submucosal injection as described herein, the "distal end" used herein refers to the portion that is far away from the operator.

U.S. Patent Application No. US20110208158A1 describes use of carboxymethyl cellulose (CMC) for submucosal injection. Carboxymethyl cellulose is a species of cellulose materials, which is significantly distinct from the modified starches used in the present invention in molecular structure and has a completely different metabolic pathway in the body from that of the modified starches used in the present invention. Starches can be degraded by amylases and amylases in the human body, while cellulose is gradually degraded by the phagocytosis of phagocytic cells in the human body. Therefore, the modified starch materials exhibit reduced local stimulation to human mucosal tissues, and can be rapidly metabolized within several hours or several days, while the cellulose materials take several weeks or even months to be completely absorbed by human tissues. That is to say, cellulose materials may cause local tissue proliferation and interfere tissue healing. Thus, the modified starch materials for submucosal injection as described herein are significantly superior to the cellulose materials.

Respective aspects of the present invention will be described in greater detail by reference to the following specific examples. Such examples merely intend to illustrate the present invention but not to limit the scope and the spirit of the present invention.

EXAMPLE 1

Composition for Submucosal Injection

This example illustrated compositions #4 to #16 for submucosal injection prepared by dispersing three exemplary biocompatible modified starches #1 to #3 as listed in Table 1 into physiological saline at various weight percentages at room temperature. Table 1 listed the physicochemical parameters of the three exemplary biocompatible modified starches used in this example. Table 2 listed the weight percentages of the biocompatible modified starches in the compositions #4 to #16 for submucosal injection and the viscosities of the compositions.

TABLE 1

| No. | Particle Size (μm) | Molecular Weight (daltons) | Water Absorbency Capability | *Viscosity (mPa · s) |
|---|---|---|---|---|
| #1 carboxymethyl starch sodium | 10-1000 | 3,000-2,000,000 | 23 | 34-3000 *the viscosity of 2% aqueous solution measured at 37° C. |
| #2 pre-gelatinized hydroxypropyl starch diphosphate | 10-1000 | 15,000-2,000,000 | 17.5 | 500-5000 *the viscosity of 6.67% aqueous solution measured at 37° C. |
| #3 cross-linked carboxymethyl starch sodium | 10-1000 | 5,000-2,000,000 | 23.5 | 10,000-100,000 * the viscosity of 2% aqueous solution measured at 37° C. |

TABLE 2

| No. | Components and Formulation | Viscosity* (mPa · s) |
|---|---|---|
| #4 | sample #1 + physiological saline: the concentration of sample #1 in physiological saline was 5 wt % | 103 |
| #5 | sample #1 + physiological saline: the concentration of sample #1 in physiological saline was 4 wt % | 57 |
| #6 | sample #1 + physiological saline: the concentration of sample #1 in physiological saline was 3 wt % | 33 |
| #7 | sample #1 + physiological saline: the concentration of sample #1 in physiological saline was 2 wt % | 20 |
| #8 | sample #1 + physiological saline: the concentration of sample #1 in physiological saline was 1 wt % | 18 |

TABLE 2-continued

| No. | Components and Formulation | Viscosity* (mPa · s) |
|---|---|---|
| #9 | sample #2 + physiological saline: the concentration of sample #2 in physiological saline was 2 wt % | 9 |
| #10 | sample #2 + physiological saline: the concentration of sample #2 in physiological saline was 3 wt % | 12 |
| #11 | sample #2 + physiological saline: the concentration of sample #2 in physiological saline was 4 wt % | 28 |
| #12 | sample #2 + physiological saline: the concentration of sample #2 in physiological saline was 5 wt % | 113 |
| #13 | sample #2 + physiological saline: the concentration of sample #2 in physiological saline was 6 wt % | 150 |
| #14 | sample #3 + physiological saline: the concentration of sample #3 in physiological saline was 0.5 wt % | 12 |
| #15 | sample #3 + physiological saline: the concentration of sample #3 in physiological saline was 1 wt % | 136 |
| #16 | sample #3 + physiological saline: the concentration of sample #3 in physiological saline was 1.5 wt % | 150 |

*The viscosity was measured at 25° C. by using a sc4-31 rotor at a rotation speed of 200 rpm.

In this example, the changes in the heights of the droplets formed by the above-mentioned compositions #4 to #16 with time were measured by a filter paper test as described below.

The filter paper test included following steps: placing a filter paper on a horizontal substrate, dropping 0.2 ml of each composition onto the filter paper with a plastic dropper, and recording the changes in the heights of the formed droplets with time. Control samples were commercially available hyaluronic acid (HA), hydroxyethyl starch (plasma substitutes, HES), and physiological saline.

The changes in the heights of the formed droplets with time as measured by the filter paper test were shown in Table 3 below.

TABLE 3

| No. | Height of the droplet at the beginning | Height of the droplet after 5 minutes | Decline Rate |
|---|---|---|---|
| #4 | 5.5 mm | 4.5 mm | 18.2% |
| #5 | 3.5 mm | 3.0 mm | 14.3% |
| #6 | 2.0 mm | 1.5 mm | 25.0% |
| #7 | 2.0 mm | 1.5 mm | 25.0% |
| #8 | 1.5 mm | 1.0 mm | 33.3% |
| #9 | 0.3 mm | 0.2 mm | 3.3% |
| #10 | 0.5 mm | 0.5 mm | 0% |
| #11 | 1.5 mm | 1.2 mm | 2.0% |
| #12 | 2.2 mm | 2.0 mm | 9.1% |
| #13 | 2.5 mm | 2.4 mm | 4.0% |
| #14 | 0.5 mm | 0.4 mm | 20% |
| #15 | 3.0 mm | 2.8 mm | 6.7% |
| #16 | 4.5 mm | 3.8 mm | 15.6% |
| *Commercially Available HA Injection | 2.5 mm | 0.5 mm | 80.0% |
| Commercially Available HES Plasma Substitutes | 1.0 mm | 0 | 100% |
| Commercially Available Physiological Saline | 0 | 0 | — |

*The viscosity of the commercially available HA injection was 198 mPa · s, which was measured at 25° C. by using a sc4-31 rotor at a rotation speed of 200 rpm.

According to the results as listed in Table 3, after the compositions for submucosal injection comprising the biocompatible modified starches and the pharmaceutically acceptable diluent (for example, physiological saline), as described herein, were added dropwise to the filter paper and absorbed by the filter paper, the heights of the droplets formed by the compositions #4 to #16 on the filter paper were much higher than those formed by commercially available HA injection, HES plasma substitutes and physiological saline. And the decline rates of the droplets formed by the compositions #4 to #16 on the filter paper were much lower than those formed by the commercially available HA injection, HES plasma substitutes and the physiological saline.

The filter paper used in the filter paper test had a porous structure, which can simulate the reticular connective tissue of the submucosa. The results of the filter paper test demonstrated that:

1) In the compositions for submucosal injection as described herein, the biocompatible modified starches were swollen in the pharmaceutically acceptable diluent rather than being dissolved, such that the swollen modified starches play a role in forming a submucosal cushion with certain height and strength.
2) Commercially available HA injection formed a droplet with a height of 2.5 mm at the beginning. However, after 5 minutes, the droplet sharply drops to 0.5 mm, indicating that the commercially available HA injection cannot effectively form a submucosal cushion with certain height and strength. Therefore, if the HA injection was used during surgery, it is not capable of forming a submucosal cushion with certain height and strength.
3) Both commercially available saline and HES plasma substitutes diffused along the gap of the filter paper. This is one of the reasons why doctors need to repeatedly perform injection during surgery.

Next, the changes in the heights of the cushions formed by the above-mentioned compositions #4 to #16 with time after submucosal injection under gastric mucosa were tested. The specific steps for test included: cutting a porcine stomach into samples with a size of about 5×5 cm and placing it on a horizontal substrate, and injecting the above compositions #4 to #16 into submucosa using an injection needle at an injection volume of 1 ml. The changes in the heights of the submucosal cushions formed after injection with time were observed and recorded. Control samples were commercially available hyaluronic acid (HA), hydroxyethyl starch (plasma substitutes, HES), and physiological saline. The test results were listed in Table 4 as below.

TABLE 4

| No. | Height of the cushions at the beginning | Height of the cushions after 30 minutes | Decline Rate |
|---|---|---|---|
| #4 | 8.0 mm | 8.0 mm | 0 |
| #5 | 7.5 mm | 7.5 mm | 0 |
| #6 | 6.5 mm | 6.5 mm | 0 |
| #7 | 5.0 mm | 5.0 mm | 0 |
| #8 | 4.5 mm | 4.5 mm | 0 |
| #9 | 4.0 mm | 4.0 mm | 0 |
| #10 | 4.5 mm | 4.5 mm | 0 |
| #11 | 5.0 mm | 5.0 mm | 0 |
| #12 | 7.5 mm | 7.5 mm | 0 |
| #13 | 8.0 mm | 8.0 mm | 0 |
| #14 | 4.0 mm | 4.0 mm | 0 |
| #15 | 7.5 mm | 7.5 mm | 0 |
| #16 | 8.0 mm | 8.0 mm | 0 |
| commercially available HA injection | 5.0 mm | 3.0 mm | 40.0% |

TABLE 4-continued

| No. | Height of the cushions at the beginning | Height of the cushions after 30 minutes | Decline Rate |
|---|---|---|---|
| commercially available HES plasma substitutes | 7.0 mm | 4.0 mm | 42.9% |
| commercially available physiological saline | 5.0 mm | 2.0 mm | 60.0% |

According to the results as listed in Table 4, the heights of the submucosal cushions formed by the compositions #4 to #16 can last for 30 minutes, while the heights of the submucosal cushions formed by the commercially available HA injection, HES plasma substitutes and physiological saline significantly dropped within 30 minutes after injection.

From the above test results for the compositions #4 to #16, the compositions were able to form a fully bulged submucosal cushions after submucosal injection, and the submucosal cushions can last sufficient time period for surgeries. Therefore, the submucosal cushions formed by the compositions for submucosal injection as described herein were beneficial for separating the lesion mucosa from the muscle layer by doctors, facilitating resection of mucosa, reducing the damage to the submucosal tissue, avoiding complications such as perforation, and inhibiting bleeding due to resection of mucosal tissue. The compositions for submucosal injection comprised biocompatible modified starches, which were swollen in an aqueous solution rather than being dissolved. Therefore, the compositions were significantly superior to other materials that were dissolved in an aqueous solution. After the compositions for submucosal injection comprising the biocompatible modified starches were injected into submucosa, free water molecules contained therein can rapidly diffuse to the surrounding tissues as free water molecules were smaller, while it was difficult for the swollen modified starch molecules to overcome the resistance to diffuse to the surrounding tissues as the swollen modified starch molecules were larger. Therefore, the height of the submucosal cushion can last sufficient time for surgery operation. If a material that was soluble in water (for example, a soluble modified starch) was used, the aqueous solution of such material upon injecting into submucosa easily diffused to the surrounding tissues along the connective tissue between the submucosa and the muscle layer due to formation of homogeneous system with water. Therefore, the height of the submucosal cushion formed by the material that was soluble in water cannot last sufficient time for surgery operation. The compositions for submucosal injection as described herein exhibited improved safety for use in vivo due to utilization of biocompatible modified starches and thus the risk of irritation of local tissues caused by use of other materials was reduced. In addition, the residual biocompatible modified starches after surgery can be rapidly degraded by amylases and/or amylases in the human body within several minutes or hours without affecting tissue healing.

EXAMPLE 2

Apparatus for Delivering the Composition for Submucosal Injection

Figure 1:
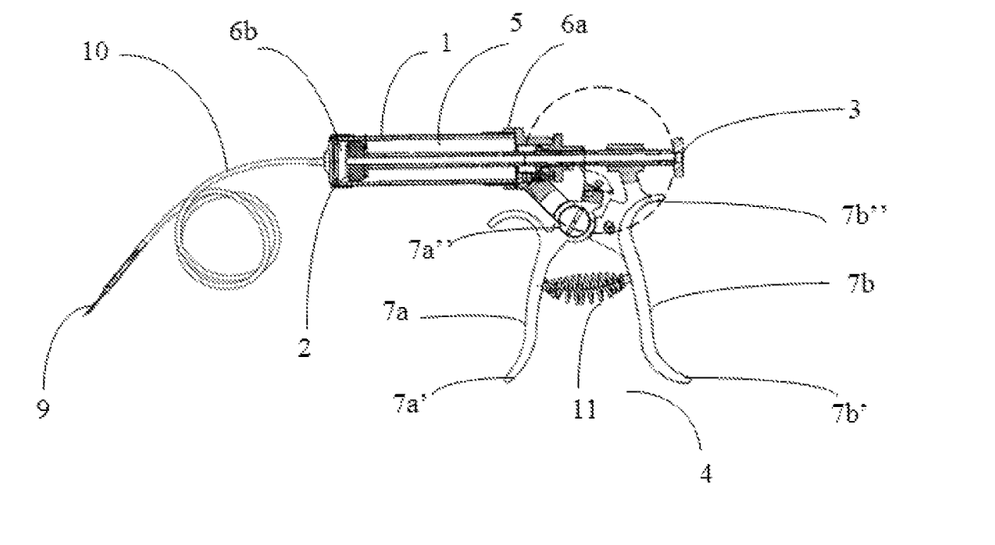
FIG. 1 is a structural schematic diagram of the apparatus for delivering the composition for submucosal injection as described herein.

As shown in FIG. 1, this example illustrated a delivery apparatus as described herein, comprising: a hollow housing 1 with a hollow portion 5 for receiving an injection agent to be delivered, and a proximal end 6a and a distal end 6b, a plunger 2 and a plunger rod 3 coupled to the plunger, and a plunger drive mechanism 4. The plunger 2 was disposed in the hollow portion 5. The plunger rod 3 is configured to drive the plunger 2 to reciprocate in the hollow portion 5, such that the composition for submucosal injection can be delivered out of the distal end 6b from the hollow portion 5. The plunger drive mechanism had a first arm 7a and a second arm 7b pivotally coupled to each other, wherein the first arm 7a and the second arm 7b had a proximal end 7a' or 7b' and a distal end 7a " or 7b ". The distal end 7a " of the first arm was coupled to the proximal end 6a of the housing, and the distal end 7b " of the second arm was coupled to the proximal end of the plunger rod. When the first arm 7a and the second arm 7b were pivoted to force the proximal end 7a' of the first arm and the proximal end 7b' of the second arm to move in a direction of facing each other, the second arm 7b forced the plunger rod 3 to drive the plunger 2 to move to the distal end 6b in the hollow portion 5. The first arm 7a was coupled to the second arm 7b by a resilient spring 11, such that the proximal ends of the first and second arms rotated in a direction of facing each other to force the plunger rod to drive the plunger to move in the hollow portion, followed by returning of the first arm and the second arm to an initial position. The plunger rod was also provided with a thread scale corresponding to the amount of formulation delivered. A catheter 10 with a needle 9 was coupled to the distal end of the hollow housing for injecting the composition for submucosal injection into the submucosa.

When using the conventional injection device and the infusion apparatus, doctors needed to operate the syringe with both hands, and thus operation was performed by multiple people at the same time with inconvenience. The delivery apparatus as described herein can be operated by one hand, and was capable of delivering a composition for submucosal injection having conveying resistance as listed in Table 5. From Table 5, the delivery apparatus as described herein can deliver the composition for submucosal injection having a viscosity that is not less than 10 mPa·s at 25° C. The plunger rod of the delivery apparatus as described herein was provided with a thread scale corresponding to the amount of the composition for submucosal injection delivered, so that accurate volume delivered by each bolus injection can be calculated according to the inner diameter of the syringe. Therefore, over-operation of the conventional injection device due to too high resistance can be avoided to accurately control injection dosage.

TABLE 5

| No. | Conveying Resistance (N) |
|---|---|
| #4 | 175 |
| #5 | 150 |
| #6 | 80 |
| #7 | 30 |
| #8 | 20 |
| #9 | 26 |
| #10 | 33 |
| #11 | 62 |
| #12 | 112 |
| #13 | 200 |
| #14 | 35 |
| #15 | 150 |
| #16 | 200 |
| Commercially Available HA Injection | 88 |
| Commercially Available HES Plasma Substitutes | 24 |

TABLE 5-continued

| No. | Conveying Resistance (N) |
|---|---|
| Commercially Available Physiological Saline | 10 |

EXAMPLE 3

Use of the Composition for Submucosal Injection as Described Herein During Resection of the Lesion Mucosa This example illustrated injection of a composition for submucosal injection comprising carboxymethyl starch sodium and physiological saline into the gastric mucosa of Bama miniature pigs and the effects thereof.
1. Composition for submucosal injection: sample #6, (3 wt % carboxymethyl starch sodium+physiological saline);
2. Animal: Bama miniature pigs, weight: 40 kg;
3. Test method: Bama miniature pigs were placed on an operation table in the supine position with general anesthesia, and then the limbs were fixed. 2 ml injection was submucosally injected directly into anterior wall of the stomach by virtue of Olympus gastroscope, and the control group accepted the same volume of physiological saline. Next, submucosal dissection was performed by incising mucosa with electrosurgical knife under gastroscope.
4. Dosage: 2 ml per injection point;
5. Administration Route: injection under gastroscope;
6. Observation Target: height and strength of submucosal cushion, and formation of submucosal edema.
7. Results:

(i) Height and Strength of Submucosal Cushion

The height of the submucosal cushion formed by the sample #6 was above 4 mm lasting for 30 minutes during surgery, and its strength completely satisfied the surgical needs. However, the strength of submucosal cushion formed by physiological saline as control group was very low and cannot meet surgical needs. Therefore, multiple injections were needed during the operation.

(ii) Submucosal Edema

No edema was observed in the experimental group of injection of sample #6. The submucosal connective tissue exhibited a clear texture and can be easily peeled off by electrosurgical knife. Significant edema was observed in control group of injection of physiological saline, and thus peeling of submucosal connective tissue by electrosurgical knife was hindered.

According to the same method, the composition #11 (4 wt % hydroxypropyl starch diphosphate+physiological saline) and the composition #14 (0.5 wt % cross-linked carboxymethyl starch sodium+physiological saline) were injected into the gastric submucosa of Bama miniature pigs, and the effects were observed.

Results:

(i) Height and Strength of Submucosal Cushion

The heights of the submucosal cushions formed by the compositions #11 and #14 were over 4 mm during the 30-minute surgery, and the strength thereof completely satisfied surgical needs. In contrast, the strength of submucosal cushion formed by physiological saline as control group was very low and cannot meet surgical needs, and thus multiple injections were needed during the operation.

(ii) Submucosal Edema

No edema was observed in the experimental groups of injection of samples #11 and #14. The submucosal connective tissue exhibited a clear texture and can be easily peeled off by electrosurgical knife. Significant edema was observed in control group of injection of physiological saline, and thus peeling of submucosal connective tissue by electrosurgical knife was hindered.

The present disclosure is described in greater detail with reference to the specific examples. These examples are merely illustrative, but not intended to limit the scope of the present invention. One having the ordinary skill in the art would understand that various modifications, changes or substitutions may be made without departing from the spirit and scope thereof. Thus, the equivalent variations according to the present invention come within the scope of the present invention.

What is claimed is:

1. A method for lifting up a first tissue layer from a second tissue layer comprising delivering a submucosal injection of a composition into the first tissue layer further comprising:
acquiring the composition, wherein the composition comprises a biocompatible modified starch in an amount ranging from 0.2 wt % to 50 wt % of a total weight of composition, which has a molecular weight from 3,000 to 2,000,000 daltons, a water absorbency capability of at least twice of its own weight, and a particle size from 500 nm to 1000 μm, wherein the biocompatible modified starch is selected from one or more of the group consisting of etherified starches comprise a carboxymethyl starch and a salt thereof, esterified starches, cross-linked starches, pre-gelatinized starches, graft starches, and composite modified starches; and a pharmaceutically acceptable carrier for injection, wherein the viscosity of the composition ranges from 9 mPa·s to 150,000 mPa·s at 25° C.

2. The method of claim 1, wherein the pharmaceutically acceptable carrier for injection is selected from one or more of the group consisting of: physiological saline, balanced salt solution, glucose solution, sterile pyrogen-free water, and glycerin.

3. The method of claim 2, wherein:
the
the cross-linked starches comprise a cross-linked carboxymethyl starch and a salt thereof;
the pre-gelatinized starches comprise a pre-gelatinized hydroxypropyl starch diphosphate;
the graft starches comprise a propylene ester-carboxymethyl starch grafted copolymer and acrylic acid-carboxymethyl starch grafted copolymer;
the composite modified starches comprise a pre-gelatinized hydroxypropyl starch diphosphate.

4. The method of claim 3, wherein the biocompatible modified starch is in an amount ranging from 0.2 wt % to 20 wt %, or 0.5 wt % to 10 wt %, or 0.5 wt % to 5 wt %, or 1 wt % to 5 wt %, or 0.5 wt % to 1.5 wt %, or 2 wt % to 6 wt % of the total weight of composition.

5. The method of claim 4, wherein the viscosity of the composition ranges from 9 mPa·s to 100,000 mPa·s, or 9 mPa·s to 10,000 mPa·s, or 9 mPa·s to 5,000 mPa·s, or 9 mPa·s to 1,000 mPa·s at 25° C.

6. The method of claim 3, wherein the biocompatible modified starch has a molecular weight ranging from 3,000 to 200,000 daltons, or 5,000 to 100,000 daltons, or 5,000 to 50,000 daltons.

7. The method of claim 3, wherein the biocompatible modified starch has a water absorbency capability from 2 to 100 times, or 5 to 75 times, or 5 to 50 times, or 2 to 10 times, or 2 to 5 times of its own weight.

8. The composition of claim 3, wherein the biocompatible modified starch has a particle size ranging from 1 μm to 500 μm, or 1 μm to 1000 μm, or 10 μm to 1000 μm.

9. The method of claim 1, wherein the biocompatible modified starch is degradable by amylases.

10. The method of claim 1, wherein
at least one of the first tissue layer or the second tissue layer comprises digestive tract mucosa, respiratory mucosa, genital tract mucosa or urinary tract mucosa and wherein:
the digestive tract mucosa comprises an esophageal mucosa or a gastrointestinal mucosa;
the respiratory mucosa comprises a nasal mucosa, a laryngeal mucosa, an oral mucosa, a tracheal mucosa or a bronchial mucosa;
the urinary tract mucosa comprises a urethral mucosa or a bladder mucosa; and
the genital tract mucosa comprises a vaginal mucosa or a uterine mucosa.

11. The method of claim 1, wherein the biocompatible modified starch is a carboxymethyl starch sodium in an amount ranging from 1 wt % to 25 wt % of the total weight of composition, and the pharmaceutically acceptable carrier for injection is physiological saline.

12. The method of claim 1, wherein the biocompatible modified starch is a hydroxypropyl starch diphosphate in an amount ranging from 0.5 wt % to 25 wt % of the total weight of composition, and the pharmaceutically acceptable carrier for injection is physiological saline.

13. The method of claim 1, wherein the biocompatible modified starch is a cross-linked carboxymethyl starch sodium in an amount ranging from 0.5 wt % to 20 wt % of the total weight of composition, and the pharmaceutically acceptable carrier for injection is physiological saline.

14. The method of claim 1, wherein:
the esterified starches comprise a carboxymethyl starch and a salt thereof;
the cross-linked starches comprise a cross-linked carboxymethyl starch and a salt thereof;
the pre-gelatinized starches comprise a pre-gelatinized hydroxypropyl starch diphosphate;
the graft starches comprise a propylene ester-carboxymethyl starch grafted copolymer and an acrylic acid-carboxymethyl starch grafted copolymer;
the composite modified starches comprise a pre-gelatinized hydroxypropyl starch diphosphate.

15. The method of claim 1, wherein the biocompatible modified starch is in an amount ranging from 0.2 wt % to 20 wt %, or 0.5 wt % to 10 wt %, or 0.5 wt % to 5 wt %, or 1 wt % to 5 wt %, or 0.5 wt % to 1.5 wt %, or 2 wt % to 6 wt % of the total weight of composition.

16. The method of claim 1, wherein the viscosity of the composition ranges from 9 mPa·s to 100,000 mPa·s, or 9 mPa·s to 10,000 mPa·s, or 9 mPa·s to 5,000 mPa·s, or 9 mPa·s to 1,000 mPa·s at 25° C.

17. The method of claim 1, wherein the biocompatible modified starch has a molecular weight ranging from 3,000 to 200,000 daltons, or 5,000 to 100,000 daltons, or 5,000 to 50,000 daltons.

18. The method of claim 1, wherein the biocompatible modified starch has a water absorbency capability from 2 to 100 times, or 5 to 75 times, or 5 to 50 times, or 2 to 10 times, or 2 to 5 times of its own weight.

19. The method of claim 1, wherein the biocompatible modified starch has a particle size ranging from 1 μm to 500 μm, or 1 μm to 1000 μm, or 10 μm to 1000 μm.

20. The method of claim 1, wherein the biocompatible modified starch is a carboxymethyl starch sodium in an amount ranging from 1 wt % to 25 wt % of the total weight of composition, and the pharmaceutically acceptable carrier for injection is physiological saline.

21. The method of claim 1, wherein the biocompatible modified starch is a hydroxypropyl starch diphosphate in an amount ranging from 0.5 wt % to 25 wt % of the total weight of composition, and the pharmaceutically acceptable carrier for injection is physiological saline.

22. The method of claim 1, wherein the biocompatible modified starch is a cross-linked carboxymethyl starch sodium in an amount ranging from 0.5 wt % to 20 wt % of the total weight of composition, and the pharmaceutically acceptable carrier for injection is physiological saline.

23. A submucosal injection composition comprising:
a biocompatible modified starch and a pharmaceutically acceptable carrier for injection, wherein the pharmaceutically acceptable carrier for injection is physiological saline,
wherein, the biocompatible modified starch is a carboxymethyl starch sodium, which has a molecular weight ranging from 3,000 to 2,000,000 daltons, a water absorbency capability of at least twice of its own weight, and a particle size from 500 nm to 1000 μm, wherein the biocompatible modified starch is degradable by amylases, and wherein the biocompatible modified starch, in an amount ranging from 1 wt % to 25 wt % of a total weight of the composition, is mixed with the pharmaceutically acceptable carrier to form a viscous composition with a viscosity ranging from 9 mPa·s to 150,000 mPa·s at 25° C.

24. The composition of claim 23, wherein the biocompatible modified starch is in an amount ranging from 1 wt % to 5 wt % or 2 wt % to 6 wt % of the total weight.

25. The composition of claim 23, wherein the viscosity of the formed viscous composition ranges from 9 mPa·s to 100,000 mPa·s, or 9 mPa·s to 10,000 mPa·s, or 9 mPa·s to 5,000 mPa·s, or 9 mPa·s to 1,000 mPa·s at 25° C.

26. The composition of claim 23, wherein the biocompatible modified starch has a molecular weight ranging from 3,000 to 200,000 daltons, or 5,000 to 100,000 daltons, or 5,000 to 50,000 daltons.

27. The composition of claim 23, wherein the biocompatible modified starch has a water absorbency capability ranging from 2 to 100 times, or 5 to 75 times, or 5 to 50 times, or 2 to 10 times, or 2 to 5 times of its own weight.

28. The composition of claim 23, wherein the biocompatible modified starch has a particle size ranging from 1 μm to 500 μm, or 1 μm to 1000 μm, or 10 μm to 1000 μm.

29. A submucosal injection composition comprising:
a biocompatible modified starch and a pharmaceutically acceptable carrier for injection, wherein the pharmaceutically acceptable carrier for injection is physiological saline,
wherein, the biocompatible modified starch is a hydroxypropyl starch diphosphate, which has a molecular weight ranging from 3,000 to 2,000,000 daltons, a water absorbency capability of at least twice of its own weight, and a particle size from 500 nm to 1000 wherein the biocompatible modified starch is degradable by amylases, and wherein the biocompatible modified starch, in an amount ranging from 0.5 wt % to 25 wt % of a total weight of the composition, is mixed with the pharmaceutically acceptable carrier to form a viscous composition with a viscosity ranging from 9 mPa·s to 150,000 mPa·s at 25° C.

30. The composition of claim 29, wherein the biocompatible modified starch is in an amount ranging from 0.5 wt % to 10 wt %, or 0.5 wt % to 5 wt %, or 1 wt % to 5 wt %, or 0.5 wt % to 1.5 wt %, or 2 wt % to 6 wt % of the total weight.

31. The composition of claim 29, wherein the viscosity of the formed viscous composition ranges from 9 mPa·s to 100,000 mPa·s, or 9 mPa·s to 10,000 mPa·s, or 9 mPa·s to 5,000 mPa·s, or 9 mPa·s to 1,000 mPa·s at 25° C.

32. The composition of claim 29, wherein the biocompatible modified starch has a molecular weight ranging from 3,000 to 200,000 daltons, or 5,000 to 100,000 daltons, or 5,000 to 50,000 daltons.

33. The composition of claim 29, wherein the biocompatible modified starch has a water absorbency capability ranging from 2 to 100 times, or 5 to 75 times, or 5 to 50 times, or 2 to 10 times, or 2 to 5 times of its own weight.

34. The composition of claim 29, wherein the biocompatible modified starch has a particle size ranging from 1 μm to 500 μm, or 1 μm to 1000 μm, or 10 μm to 1000 μm.

35. A submucosal injection composition comprising:
a biocompatible modified starch and a pharmaceutically acceptable carrier for injection, wherein the pharmaceutically acceptable carrier for injection is physiological saline,
wherein, the biocompatible modified starch is a cross-linked carboxymethyl starch sodium, which has a molecular weight ranging from 3,000 to 2,000,000 daltons, a water absorbency capability of at least twice of its own weight, and a particle size from 500 nm to 1000 μm, wherein the biocompatible modified starch is degradable by amylases, and wherein the biocompatible modified starch, in an amount ranging from 0.5 wt % to 20 wt % of a total weight of the composition, is mixed with the pharmaceutically acceptable carrier to form a viscous composition with a viscosity ranging from 9 mPa·s to 150,000 mPa·s at 25° C.

36. The composition of claim 35, wherein the biocompatible modified starch is in an amount ranging from 0.5 wt % to 10 wt %, or 0.5 wt % to 5 wt %, or 1 wt % to 5 wt %, or 0.5 wt % to 1.5 wt %, or 2 wt % to 6 wt % of the total weight.

37. The composition of claim 35, wherein the viscosity of the formed viscous composition ranges from 9 mPa·s to 100,000 mPa·s, or 9 mPa·s to 10,000 mPa·s, or 9 mPa·s to 5,000 mPa·s, or 9 mPa·s to 1,000 mPa·s at 25° C.

38. The composition of claim 35, wherein the biocompatible modified starch has a molecular weight ranging from 3,000 to 200,000 daltons, or 5,000 to 100,000 daltons, or 5,000 to 50,000 daltons.

39. The composition of claim 35, wherein the biocompatible modified starch has a water absorbency capability ranging from 2 to 100 times, or 5 to 75 times, or 5 to 50 times, or 2 to 10 times, or 2 to 5 times of its own weight.

40. The composition of claim 35, wherein the biocompatible modified starch has a particle size ranging from 1 μm to 500 μm, or 1 μm to 1000 μm, or 10 μm to 1000 μm.

* * * * *